Oct. 29, 1968 MASAMI UTSUMI Plant Pat. 2,843

RED POINSETTIA PLANT

Filed March 20, 1967

INVENTOR
MASAMI UTSUMI

BY Rummler & Snow
Att'ys

United States Patent Office

Plant Pat. 2,843
Patented Oct. 29, 1968

2,843

RED POINSETTIA PLANT

Masami Utsumi, 3701 Prescott Ave.,
Lincoln, Nebr. 68506

Filed Mar. 20, 1967, Ser. No. 624,637
1 Claim. (Cl. Plt.—86)

ABSTRACT OF THE DISCLOSURE

This disclosure concerns a new and distinct variety of red poinsettia plant, characterized by the very large size and number of its deep red bracts which grow on relatively short petioles so that the involucre is nearly closed below the inflorescence to present a solid face 11 to 12 inches in diameter disposed in a substantially horizontal plane, distinguished by the fact that the bracts are individually twisted about a horizontal axis to overlap each other in a somewhat shingle fashion, and by the excellent tolerance of the bracts and foliage to adverse store and consumer home temperature changes.

*Background of the invention*

This new variety of poinsettia plant was originated by me as the result of extensive breeding effort carried on at my greenhouses in Lincoln. Nebr. since 1956, with the object of developing an improved poinsettia plant having better bract and foliage retention characteristics, a more striking and attractive display of the bract involucre, and better tolerance of adverse temperature changes. These characters were sought for a semidwarf variety of poinsettia that would average about 15 inches in height for the mature plant when cultivated under normal procedures for glass house production.

This new variety, which originated as a seedling produced by crossing Ecke White (P.P. 1,802) as the seed parent and an unnamed and unpatented red seedling selected from a mixed group of seedlings resulting from numerous crossings of Ecke White with various other varieties, was observed by me to have the above advantages as well as several other desirable characteristics and was, therefore, selected by me for propagation and further investigation. Now, as the result of extensive asexual propagation of this new variety at Lincoln, Nebr., I have found that each generation comes true to form and that the aforesaid characteristics are established and are transmitted true to form from generation to generation.

*Description of the drawing*

My new variety of poinsettia plant is shown in the accompanying full color drawings in which—

*Description of the new plant variety*

Figure 1:
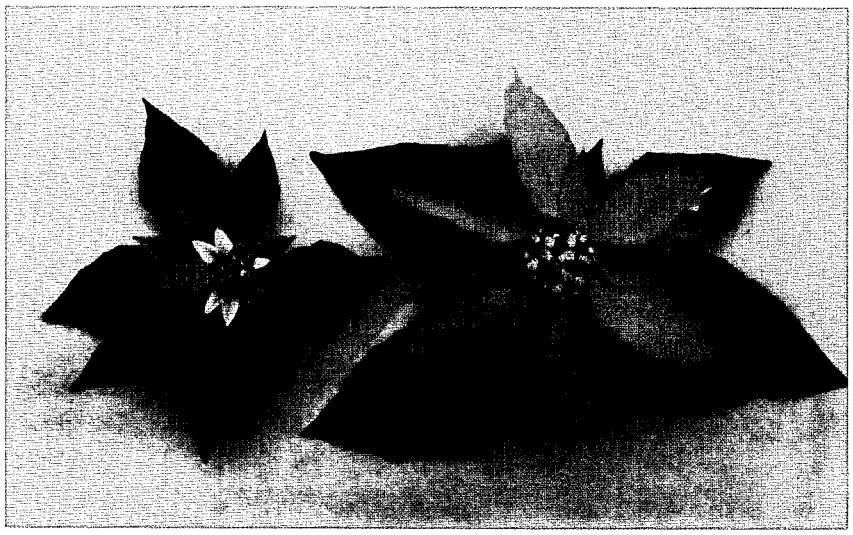
FIG. 1 is a top plan view showing the young plant as the bracts are beginning to develop, and showing the fully developed mature plant with its dark green foliage.
Figure 2:
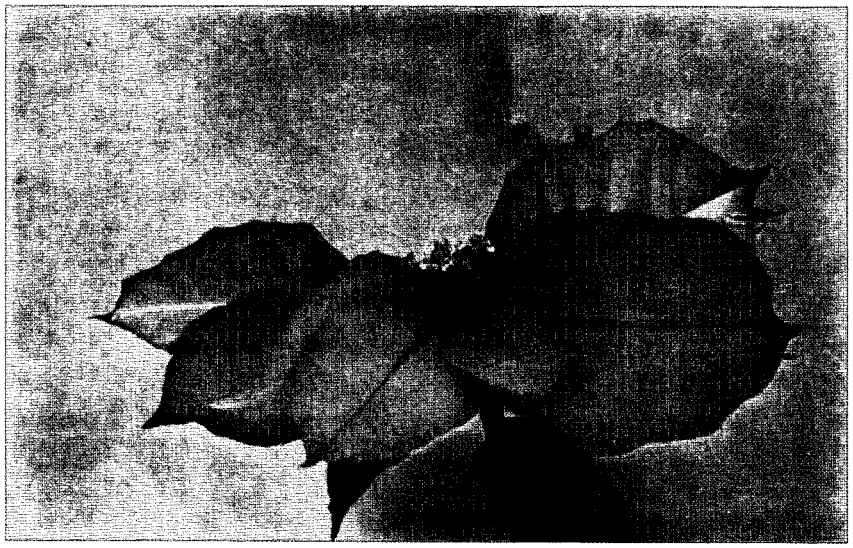
FIG. 2 is a side view of the mature plant showing the substantially horizontal display of the bracts, their overlapping disposition, and the characteristic 30 to 45 degree twist of the mature bract, each about its own substantially horizontal axis.

The following is a detailed description of my new variety of poinsettia with the color designations according to the Horticultural Color Chart of the British Color Council:

Origin: Seedling.
Parentage:
*Seed parent.*—Ecke White (P.P. 1,802).

*Pollen parent.*—An unnamed red seedling (unpatented) from an unknown cross with Ecke White.
Classification:
*Botanic.—Euphorbia pulcherrima.*
*Commercial.*—Poinsettia.
Form: Shrubs.
Growth: Upright, vigorous and rapid.
Height: 12 to 18 inches, averaging about 15 inches.
Strength: Excellent and sturdy.
Branching: None, unless decapitated.
Foliage:
*Leaves.*—Abundant, 10 to 12 per stalk. Size—4¼ to 6½ inches long by about 2 to 4 inches wide. Shape—ovate and elliptic with entire margin. Texture—smooth. Color: young leaves—Fern Green o862 to Sprinach Green o960; mature leaves—approximately Willow Green ooo862. Petioles—length, 2 to 2⅜ inches; color—red. Ribs and veins—pinnate and prominent and of light color in open leaves, dark and less distinct in mature leaves.
*Bracts.*—Number—20 to 25. Size—about 2¾ to 5½ inches long by about 1¼ to 2⅜ inches wide. Shape—generally elliptic with acuminate tip and entire margin. Arrangement—generally overlapping with involucre spread of about 10½ to 12 inches in diameter. Color—same as in U.S.D.A. "Stoplight." Appearance—velvety. Petioles—short, red in color.
*Persistence.*—Excellent. Leaves persist from base to bracts; and bracts and inflorescence persists on the plant for 2 to 2½ months.
*Effect of temperature change.*—Plant is grown only in controlled environment but is very hardy and is tolerant of normally adverse temperature changes occurring in retail stores and homes.
*Disease resistance.*—Resistant to root rot, bacterial canker and leaf spot, as tested at Lincoln, Nebr., under conditions where such diseases were present in other plants.
Blooms: Once each year in late fall. The flowers are cymose, each with a single terminal anther 0.3 mm. long, and 5 mm. long filaments of deep red color. The pollen is yellow in color and each flower has a single pistil 5 mm. long. The stigmas are of dark red color and the ovaries are three-parted with central placenta.

The bract and foliage retention ability of my new variety is particularly favorable, fully equal to that of "Mikkelpink" (P.P. 2,501) and extensive propagation of the new variety shows the foliage persistence, from base to bracts, to be like that of "Paul Mikkelsen" (P.P. 2,328). The large bract formation is like "Indianapolis Red" (P.P. 1,068) and an outstanding characteristic of the new variety is the overlapping and horizontal disposition of the bracts with their 30 to 45 degree twist at the petioles and about the axes of their central spines.

The foliage of the new variety of poinsettia is very favorably tolerant of adverse retail store and consumer home temperature variations, which factor is of great commercial advantage in that the foliage retention ability allows the retailer and wholesaler to initiate a longer selling program. Other commercial advantages of the new variety are to be found in the fact that stock plants will branch easily, if decapitated, to provide an abundant supply of cuttings for asexual propagation by conventional vegetative cutting procedures and the cuttings form an opulent root structure within 10 to 14 days in the manner of "Ecke Pink" (unpatented). Also, no growth retardant is required for the plant to reach its average full height of about 15 inches in the natural course of its growth under standard green house environment.

I claim:

1. A new and distinct variety of red poinsettia plant substantially as shown and described, characterized by its very large and showy bracts which overlap each other laterally to present a closed involucre closely surrounding the inflorescence, by the 30 to 45 degree twist of the individual bracts on their petioles, by the large diameter of the involucre and its substantially horizontal disposition, by its tolerance of adverse temperature changes without dropping of leaves or bracts, and by the abundance of its foliage which persists from base to inflorescence for a relatively long period.

No references cited.

ROBERT E. BAGWILL, *Primary Examiner*.